(12) United States Patent
Wu et al.

(10) Patent No.: US 10,384,002 B2
(45) Date of Patent: Aug. 20, 2019

(54) SENSOR PATCH, SYSTEM, AND METHOD FOR DETECTING FLUID LEAKAGE

(71) Applicants: National Taipei University of Technology, Taipei (TW); Chih-Jen Wu, Taipei (TW)

(72) Inventors: Chih-Jen Wu, Taipei (TW); Jung-Tang Huang, Taipei (TW)

(73) Assignees: MACKAY MEMORIAL HOSPITAL, Taipei (TW); NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 128 days.

(21) Appl. No.: 15/541,711

(22) PCT Filed: Jan. 30, 2015

(86) PCT No.: PCT/CN2015/071939
§ 371 (c)(1),
(2) Date: Jul. 6, 2017

(87) PCT Pub. No.: WO2016/119211
PCT Pub. Date: Aug. 4, 2016

(65) Prior Publication Data
US 2018/0001021 A1    Jan. 4, 2018

(51) Int. Cl.
*A61M 1/00* (2006.01)
*A61M 5/00* (2006.01)
(Continued)

(52) U.S. Cl.
CPC ...... *A61M 5/16831* (2013.01); *A61M 1/3656* (2014.02); *A61M 5/14248* (2013.01); *A61M 2205/15* (2013.01)

(58) Field of Classification Search
CPC ........ A61M 1/00; A61M 1/3656; A61M 5/00; A61M 5/14248; A61M 5/16831;
(Continued)

(56) References Cited

U.S. PATENT DOCUMENTS 4,193,068 A * 3/1980 Ziccardi ............. A61B 5/02042
                                                      200/52 R
4,374,379 A * 2/1983 Dennison, Jr. ......... G08B 21/20
                                                      174/117 A
(Continued)

FOREIGN PATENT DOCUMENTS

FR          2826726 A1 *  1/2003  ............ G01M 3/045

*Primary Examiner* — Nguyen Q. Ha (57) ABSTRACT

A sensor patch, system, and method for detecting a fluid leaked from a target site of a subject are provided. The sensor patch (100) includes a first detecting unit (127), a second detecting unit (128), and a patch body (110). The first detecting unit (127) includes a first pair of sensors (120A) respectively having a first end (121A) configured to be placed approximating the target site, while the second detecting unit (128) includes a second pair of sensors (120B) respectively having a first end (121B) configured to be placed away from the target site. Each sensor includes a conductive wire (125) and an insulating sheath (126) encapsulating the conductive wire (125) in a manner that a portion of the first end (121A, 121B) of the conductive wire (125) is exposed yet without directly contacting the subject's skin. The patch body (110) has an adhesive surface (104) for securing the first and second detecting units (127, 128) to the subject. The sensor patch enhances the detection specificity.

29 Claims, 4 Drawing Sheets

(51) Int. Cl.
*A61M 37/00* (2006.01)
*A61M 99/00* (2012.01)
*G01M 3/04* (2006.01)
*G01M 3/40* (2006.01)
*G08B 21/20* (2006.01)
*A61M 5/168* (2006.01)
*A61M 5/142* (2006.01)
*A61M 1/36* (2006.01)

(58) Field of Classification Search
CPC .. A61M 37/00; A61M 99/00; A61M 2205/15; G01M 3/04; G01M 3/045; G01M 3/40; G08B 21/20
See application file for complete search history.

(56) References Cited

U.S. PATENT DOCUMENTS

| | | | | |
|---|---|---|---|---|
| 5,947,910 A * | 9/1999 | Zimmet | ............ | A61M 5/16836 600/547 |
| 5,964,703 A * | 10/1999 | Goodman | .......... | A61M 5/16836 600/382 |
| 6,461,329 B1 * | 10/2002 | Van Antwerp | .... | A61M 5/16836 604/111 |
| 8,217,218 B2 * | 7/2012 | Court | .................. | A61M 1/3653 340/605 |
| 8,646,318 B2 * | 2/2014 | Yu | ......................... | G01M 3/165 137/15.11 |
| 8,696,571 B2 * | 4/2014 | Marttila | ............ | A61M 5/16836 600/371 |
| 8,981,948 B2 * | 3/2015 | Olde | .................... | A61B 5/0416 340/605 |
| 9,480,455 B2 * | 11/2016 | Buckberry | ............... | A61B 7/04 |
| 2002/0198483 A1 * | 12/2002 | Wariar | .................. | A61M 5/158 604/5.01 |
| 2009/0301172 A1 * | 12/2009 | Raymond | ............. | G01M 3/165 73/40 |
| 2010/0100026 A1 * | 4/2010 | Morris | ................ | A61M 1/3653 604/5.04 |
| 2015/0374896 A1 * | 12/2015 | Du | ...................... | A61M 1/3656 604/111 |
| 2017/0333615 A1 * | 11/2017 | Du | ...................... | A61M 1/3656 |

* cited by examiner

SENSOR PATCH, SYSTEM, AND METHOD FOR DETECTING FLUID LEAKAGE

BACKGROUND OF THE INVENTION

1. Field of the Invention

The present disclosure relates to the detection of fluid leakage occurring at a target site of a subject. More particularly, the disclosed invention relates to a sensor patch, system, and method for detecting said fluid leakage.

2. Description of Related Art

Wounds caused by surgical procedures or traumas are often stitched or closed by other means. However, the closed wounds are prone to open, leading to bleeding at the wounds. In the case where the wounds are covered by dressings or the patients are unconscious or otherwise unable to be aware of the bleeding, it may take a long time before the caretaker or the patient notices the bleeding. This may result in excessive blood loss, which may jeopardize the patient's recovery process.

Moreover, in the clinical setting, procedures for the injection of fluid into the human body and the withdrawal of body fluid from the human body are quite common. For example, medicines or other substances are often delivered to the body via intravenous infusion (drip infusion), while various kinds of body fluids (such as, blood, cerebrospinal fluid, ascites and pleural effusion) are withdrawn from the body. In some cases (e.g., dialysis), the withdrawn body fluid may be processed and then returned to the body. These applications involve the use of a syringe needle being pricked into a human body. During the period in which the syringe needle stays in the patient's body, the fluid being delivered or withdrawn may leak from the patient's vein or the mispositioned needle, or the tissue surrounding the needle may bleed. The leaked fluid, if not attended to properly, will damage the tissue around the injection site, which is known as extravasation. Depending on the medication, amount of exposure, and location, extravasation can potentially cause serious injury and permanent harm, such as tissue necrosis. Milder consequences of extravasation include irritation, characterized by symptoms of pain and inflammation, with the clinical signs of warmth, erythema, or tenderness.

Injection fluids containing vesicant and/or irritative substances often aggravate the extravasation. Examples of highly vesicant drug substances include chemotherapeutic agents (such as adriamycin and vincristine), vasopressor agents (e.g., dopamine), contrast agents, hypertonic glucose solutions, electrolyte solutions (such as potassium chloride, calcium chloride, and sodium bicarbonate solutions), phenytoin, and total parenteral nutrition (TPN) solutions. These drugs are often administered using an infusion pump with an alarm. However, according to survey conducted by Pennsylvania Patient Safety Advisory in 2007, the alarm signal was only activated in half of the total leakage cases.

In view of the foregoing, fluid leakage is a longstanding issue that nevertheless still needs addressing.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a sensor patch. The sensor patch can be arranged to cover a target site of a subject and used to detect a fluid leaked from the target site.

According to one embodiment of the present disclosure, the sensor patch comprises a first detecting unit, a second detecting unit, and a patch body. The first detecting unit includes a first pair of sensors respectively having a first end configured to be placed at a first position approximating the target site, while the second detecting unit includes a second pair of sensors a first end configured to be placed at a second position away from the target site. Each sensor includes a conductive wire and an insulating sheath encapsulating the conductive wire in a manner that a portion of the first end of the conductive wire is exposed without being in direct contact with the subject's skin. The patch body has an adhesive surface for securing the first and second detecting units to the subject.

According to some embodiments of the present disclosure, the first ends of the two sensors in the first or second detecting unit are spaced apart by 2.5 to 7.5 millimeters; preferably, 5 millimeters.

According to certain embodiments of the present disclosure, the portion of the conductive wire that is exposed has a length ranging from 2.5 to 7.5 millimeters; preferably, 5 millimeters.

In some embodiments, the distance between the first position and the second position is 1 to 5 centimeters.

In certain embodiments, the thickness of the insulating sheath is 0.1 to 0.5 mm; preferably 0.3 mm.

According to optional embodiments of the present disclosure, the first detecting unit further comprises a first connector electrically coupled to the respective second ends of the first pair of sensors, and the second detecting unit further comprises a second connector electrically coupled to the respective second ends of the second pair of sensors.

Still optionally, the present sensor patch may further comprise a release sheet attached to the adhesive surface of the patch body.

In various embodiments of the present disclosure, the fluid is blood or an infusion solution. According to certain optional embodiments, the infusion solution comprises a therapeutic drug.

According to optional embodiments of the present disclosure, the sensor patch may further comprise a frame that is attached to the other surface of the patch body and disposed along at least a portion of the peripheral of the patch body. In certain embodiments, the frame is disposed along the peripheral of the patch body.

According to some embodiments of the present disclosure, the patch body is made from a waterproof, transparent film. Alternatively, or additionally, the present patch body is air and vapor-permeable.

In another aspect, the present disclosure is directed to a system for detecting a fluid leaked from a target site of a subject.

According to one embodiment of the present disclosure, the system comprises a sensor patch according to any of the above-mentioned aspect/embodiments, a wearable detection device, and an alarm device. The first or second detecting unit of the sensor patch, when being conducted, is configured to generate a first electric signal or a second electric signal. The wearable detection device comprises a power supply, a processing unit, and a wireless communication unit. The processing unit is electrically coupled to the power supply and the first ends of the sensors of the sensor patch, and is configured to receive the first electric signal and/or the second electric signal. The processing unit is also configured to determine the impedance of the first and/or second electric signals, and generate a leak signal when (1) the impedance of the first electric signal is no less than a threshold, and (2) the second electric signal impedance of the is less than the threshold or the second electric signal is absent. The wireless communication unit is electrically coupled to the power supply and the processing unit, and is configured to send out the leak signal upon receiving the leak signal from the processing unit. The alarm device is communicatively coupled to the wireless communication unit, and is configured to generate an alarm upon receiving the leak signal from the wireless communication unit.

According to certain embodiments of the present disclosure, the first detecting unit further comprises a first connector electrically coupled to the respective second ends of the first pair of sensors, while the second detecting unit further comprises a second connector electrically coupled to the respective second ends of the second pair of sensors coupled; and the wearable detection device further comprises two sockets for respectively accommodating the first and second connectors.

In certain embodiments, the present wearable detection device may further comprise a substrate, on which the power supply, the processing unit, and the wireless communication unit are surface mounted.

Still optionally, the present wearable detection device may further comprise an analog to digital converter, operational amplifier, and/or pulse-width modulator that is electrically coupled to the processing unit.

In certain embodiment, the analog to digital converter is configured to convert the first electric signal or the first and second electric signals into a third electric signal; and the processing unit is configured to determine the output voltage (Vo) of the third electric signal, and determines the type of the liquid that is leaked based on the output voltage.

According to various embodiments of the present disclosure, the processing unit is a microprocessor, microcontroller, digital signal processor, application specific integrated circuit (ASIC), or field programmable gate array (FPGA).

According to some embodiments of the present disclosure, the wireless communication unit is a Bluetooth module, Bluetooth smart module, near field communication (NFC) module, microelectromechanical system (MEMS)-based module, WIFI module, radio frequency (RF) module, or radio frequency identification (RFID) module.

In certain embodiments, the alarm device is a multimeter, personal digital assistant (PDA), personal computer (PC), notebook, tablet computer, or smart phone.

In certain embodiments, the present alarm device may further comprise a user interface, which is configured to present the alarm to a user and/or receive an input from the user.

In some embodiments, the present system may further comprise a carrier, which is configured to accommodate the wearable detection device, and be worn around a body part of the subject.

In still another aspect, the present disclosure is directed to a method for detecting a fluid leaked from a target site of a subject by use of the system according to the above-mentioned aspect/embodiments of the present disclosure. In this case, the respective first ends of the first pair of sensors are placed at the first position, the respective first ends of the second pair of sensors are placed at the second position, and the wearable detection device is worn by the subject.

According to certain embodiments of the present disclosure, the method comprises the steps as follows. The first and/or second electric signals transmitted from the first and/or second detecting units are received by the processing unit, and then the respective impedances of the first and/or second electric signal are determined by the processing unit. A leak signal is generated by the processing unit when (1) the first electric signal is no less than a threshold, and (2) the second electric signal is less than the threshold or the second electric signal is absent. The leak signal is transmitted to the alarm device by the wireless communication unit. An alarm is sent by the alarm device based on the leak signal.

In various embodiments of the present disclosure, the fluid is blood or an infusion solution. According to certain optional embodiments, the infusion solution comprises a therapeutic drug.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIGS. 4A and 4B are respectively a block diagram and a schematic diagram according to one embodiment of the present disclosure, in which FIG. 4A illustrates a wearable detection device and an alarm device of a system, and FIG. 4B illustrates a carrier of a system that is worn around the arm of a subject and has a wearable detection device accommodated therein.

In accordance with common practice, the various described features/elements are not drawn to scale but instead are drawn to best illustrate specific features/elements relevant to the present invention. Also, like reference numerals and designations in the various drawings are used to indicate like elements/parts.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. As used herein, the term "about" generally means values within 10%, 5%, 1%, or 0.5% of a given value or range. Alternatively, the term "about" means values within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "fluid leakage" refers to any leak and/or moisture at or around a target site of a subject. For example, the target site may locate at a wound of a subject, and the fluid may be the blood or other body fluid leaked from the wound. Alternatively, the target site can be a site at which fluid (such as, blood or other body fluid, water, and solutions containing drugs, antibiotics or other substances) is being removed from or returned to and/or infused into a subject, and in these circumstances, the fluid leakage often occurs at the needle insertion site.

Throughout the present disclosure, the term "subject" or "patient" refers to an animal including the human species that can be subject to the sensor patch, detection system, and detection method of the present invention. The term "subject" or "patient" intended to refer to both the male and female gender unless one gender is specifically indicated.

Here, the detection results are divided into four categories depending on the actual condition and the detection outcome. Specifically, a test result is true positive when a fluid leakage condition is correctly identified by the claimed system. A false positive result, on the other hand, means the system incorrectly identified a non-leakage condition as a positive outcome. When a fluid leakage condition is not detected by the system, it is a false negative result. In the case of a true negative result, the system correctly determines that there is no fluid leakage occurring at the target site.

In the present disclosure, the term "detection sensitivity" refers to the ability to identify a fluid leakage condition correctly, and as such, it is defined as the number of true positives divided by the total number of fluid leakage conditions (that is, the sum of true positives and false negatives). As could be appreciated, an increase of the false negatives or a decrease of true positive results in the decrease of the detection sensitivity. On the other hand, the term "detection specificity" refers to the ability to exclude a fluid leakage condition correctly, and hence, it is expressed as the number of true negatives divided by the total number of non-leakage cases (i.e., the sum of true negatives and the false positives). As such, a decrease of true negatives or an increase of false positives decreases the detection specificity.

In order to detect the fluid leakage condition more accurately and to reduce the false positive results, such as those caused by sweating, the present disclosure provides a sensor patch having two detecting units respectively comprising a pair of sensors. Accordingly, the first aspect of the present disclosure is a sensor patch, which, when being applied onto a subject's body, can be used to detect fluid leakage occurring at a target site covered by the sensor patch.

Figure 1:
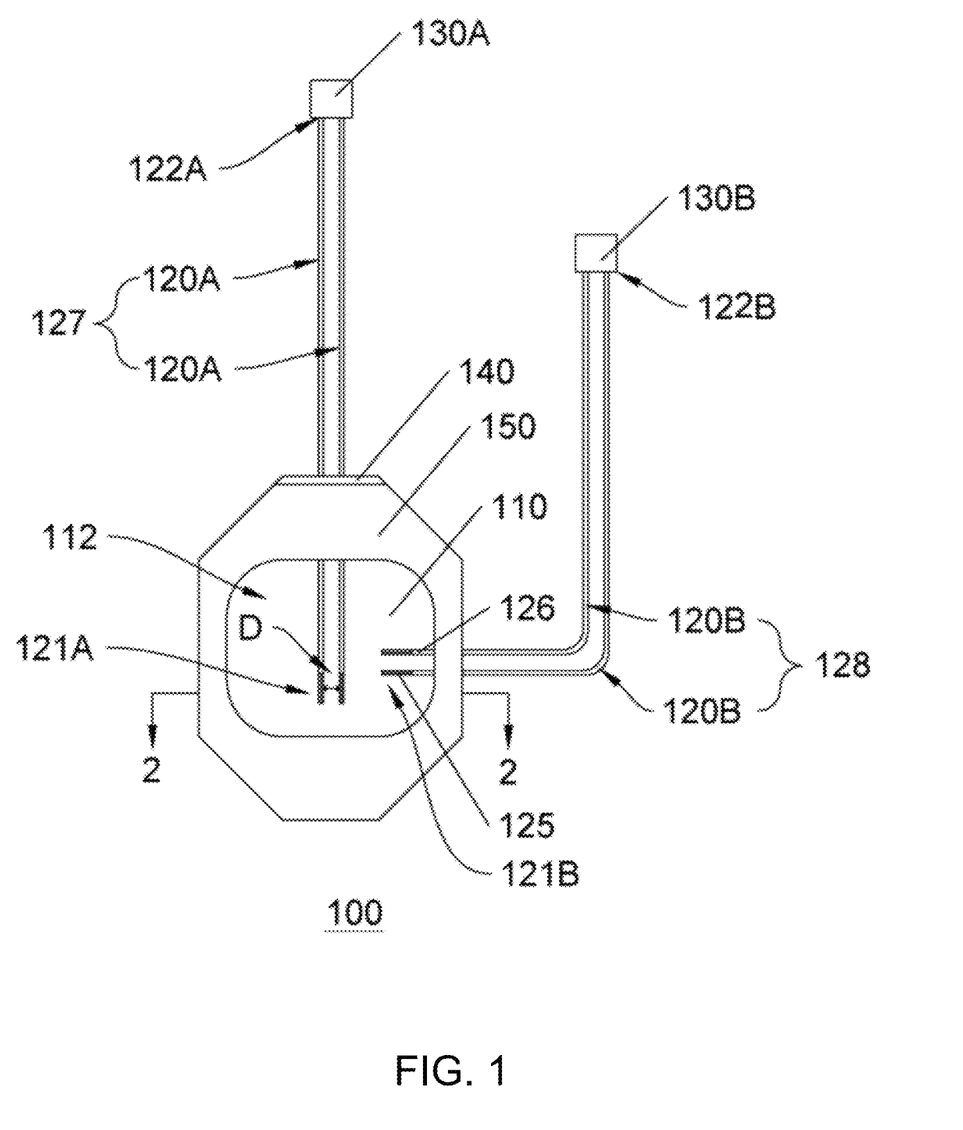
FIG. 1 is a schematic diagram illustrating the a sensor patch according to one embodiment of the present disclosure.

The structure of a sensor patch 100 according to one embodiment of the present disclosure is discussed below in connection with both the schematic diagram of FIG. 1 and the sectional view of FIG. 2, which is taken along line 2-2 in FIG. 1. As illustrated in FIG. 1, the sensor patch 100 comprises a patch body 110, a first detecting unit 127, and a second detecting unit 128.

The patch body 100 has a non-adhesive surface 102 and an adhesive surface 104. The adhesive surface 104 is used for securing the first detecting unit 127 and the second detecting unit 128 to the subject.

In certain embodiments, the patch body is made from a transparent film (including transparent thin films). Alternatively, the patch body is made from a non-transparent film, such as conventional bandages and Band-Aids. In certain optional embodiments, the patch body is waterproof and/or air and vapor-permeable.

The first detecting unit 127 has two sensors 120A each having a first end 121A and a second end 122A. Similarly, the second detecting unit 128 also has two sensors 120B respectively having a first end 121B and a second end 122B. Each of the sensors 120A and 120B comprises a conductive wire 125, and an insulating sheath 126 encapsulating the conductive wire 125 in a manner that a portion of the conductive wire at the first end of the sensor is exposed yet without being in direct contact with the subject's skin. For the brevity of description, only the first detecting unit 127 is discussed herein, however, the reader is reminded that the same description applies to the second detecting unit 128 as well. Also, for the purpose of discussion, each sensor is divided into an upper portion and a lower portion. As illustrated in FIG. 2, the upper portion 123 of the first end 121A of the sensor 120A is not encapsulated by the insulating sheath 126 and is facing the adhesive surface 104 of the patch body 110, whereas the lower portion 124 of the first end 121A of the sensor 120A is encapsulated by the insulating sheath 126 which is in direct contact with the skin of the subject while the sensor patch 100 is in use.

Figures 2, 3:
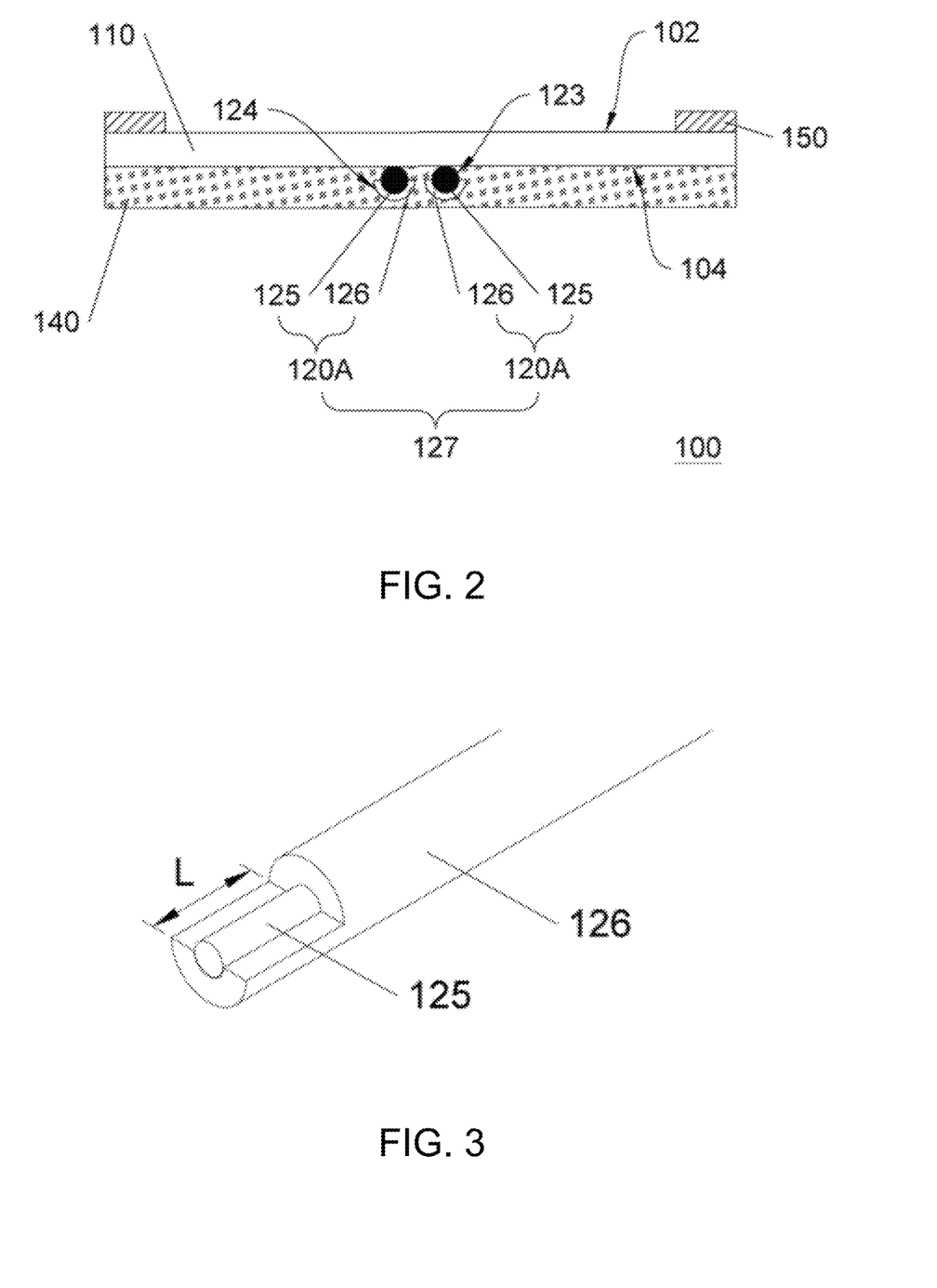
FIG. 2 is a sectional view of the sensor patch taken along line 2-2 in FIG. 1.
FIG. 3 is a partial enlargement view illustrating the first end of a sensor according to one embodiment of the present disclosure.

See, also FIG. 3, which is a partial enlargement view of the sensor 120A in FIG. 1. The part of the conductive wire 125 at the upper portion 123 of the first end 121A is not encapsulated by the insulating sheath 126; in this way, the exposed part of the conductive wire 125 can be used for detecting the fluid leakage. On the other hand, the remaining part of the conductive wire 125 is encapsulated by the insulating sheath 126. Since the conductive wire 125 is not in direct contact with the subject's skin, any interferences caused by the noise signals resulted from the subject's skin condition (e.g., the noise signal resulted from sweating) may be minimized.

The present design of partially exposed conductive wire is also advantageous in that the false positive detection rate may be reduced when the present sensor patch is employed for the detection of any leaked fluid such as during an IV infusion process. For example, at the first end 121A of each sensor 120A, the lower portion 123 of the conductive wire 125 is encapsulated by the insulating sheath 126. Thus, the pair of sensors 120A will not be easily conducted due to the minor amount of sweat or moist present at or around the target site, thereby reducing the incidents of false positive detection. Rather, the amount of fluid present at or around the target site must exceed a certain level, such as until the exposed part of the conductive wire 125 is covered by the accumulated fluid, so that the two sensors 120A of the first detecting unit 127 are conducted. To do so, the dimensions of the exposed and encapsulated parts of the conductive wire 125 needs to be carefully designed so that the intended function thereof is achieved with high sensitivity/specificity. According to various embodiments of the present disclosure, the portion of the conductive wire 125 that is exposed has a length L ranging from about 2.5 to 7.5 millimeters; for example, 2.5, 3, 3.5, 4, 4.5, 5, 5.5, 6, 6.5, 7, or 7.5 millimeters. According to certain embodiments of the present disclosure, the thickness of the insulating sheath 126 is about 0.1 to 0.5 millimeters; preferably, 0.3 millimeters.

To assure the desired detection specificity, the distance D between the two first ends 121A of the first pair of sensors 120A in the first detecting unit 127 is preferably about 2.5 to 7.5 millimeters. According to various embodiments of the present disclosure, the distance D can be 2.5, 3, 3.5, 4, 4.5, 5, 5.5, 6, 6.5, 7, or 7.5 millimeters. As is evidenced from the working examples provided below, paired sensors spaced apart by a distance greater than the above specified range will not become conducted under the test condition, thereby lowering the true positive detecting rate and increasing the false negative detecting rate.

During use, the respective first ends 121A of the sensors 120A in the first detecting unit 127 are placed at a first position in close proximity to the target site, while the first ends 121B of the sensors 120B in the second detecting unit 128 are placed at a second position away from the target site. As could be appreciated, the leaked fluid mostly leaks from the target site and then spreads outwardly from the target site. By disposing the first detecting unit 127 and second detecting unit 128 appropriately relative to the location of the target site, the first detecting unit 127 would become conducted sooner than that of the second detecting unit 128 in the case of fluid leakage. Sweating, on the other hand, does not often starts at a particular point only; rather, it occurs across a certain arear of the subject's body surface. Therefore, in the case of excessive sweating, both the first and second detecting units 127 and 128 would become conducted at substantially the same time. In this way, the present sensor patch 100, while being used in the fluid leakage detection, is able to discriminate the fluid leakage condition and the sweating, thereby enhancing the detection specificity. In view of the foregoing, the relative disposition between the first detecting unit 127 and the second detecting unit 128 is important to the present sensor patch 100. According to various embodiments of the present disclosure, the distance between the first ends 121A of paired sensors 120A in the first detecting unit 127 and the first ends 121B of paired sensors 120B in the second detecting unit 128 is about 1 to 5 centimeters; such as 1, 1.5, 2, 2.5, 3, 3.5, 4, 4.5, or 5 centimeters. In other word, the distance between the afore-mentioned first position and second position, while the sensor patch 100 is in use, is about 1 to 5 centimeters.

In some embodiments, the sensor patch 100 further comprises two connectors 130A and 130B. The first connector 130A is electrically coupled to the respective second ends 122A of the paired sensors 120A in the first detecting unit 127. Similarly, the second connector 130B is electrically coupled to the respective second ends 122B of the paired sensors 120B in the second detecting unit 128.

Still optionally, the sensor patch 100 may further comprise a release sheet 140 attached to the adhesive surface 104 of the patch body 110. The release sheet is used to protect the adhesive surface 104 of the patch body 110 against dirt or dust. The release sheet 140 is removed during use to expose the adhesive surface 104, so that the patch body 110 can be applied onto the subject's skin.

According to optional embodiments of the present disclosure, the sensor patch 100 may further comprise a frame 150. The frame 150 is attached to the non-adhesive surface 102 of the patch body 110 and disposed along at least a portion of the peripheral of the patch body 100. The frame 150 is provided to maintain the integrity of the sensor patch's shape before it is applied to the subject's skin. The frame 150 also keeps the patch body 110 from folding over itself or wrinkling as one applies it. The frame 150 may optionally be removed upon the application of the sensor patch 100; alternatively, the frame 150 may be left on the patch body 110. As illustrated in FIG. 1, the frame 150 is disposed along the entire peripheral of the patch body 110; however, the claimed invention is not limited thereto. Rather, in certain embodiments, only a portion of the peripheral of the patch body is disposed with the frame.

In certain optional embodiments, the patch body 110 is provided with a transparent observing window 112, and the first ends 121A and 121B of each of the sensors 120A and 120B are all disposed within the transparent observing window 112. The transparent observing window 112 allows the health caretaker to observe/monitor the condition of the target site with naked eyes. As illustrated in FIG. 1, the patch body 110 is transparent, and the transparent observing window 112 is defined by the frame 150. In alternative cases, the patch body 110 may be non-transparent, and a portion of the patch body 110 can be carved out and replaced with a transparent film thereby forming the transparent observing window.

According to various embodiments of the present disclosure, the sensor patch 100 can be used in a fluid leakage detection process, such as for the detection of blood leaked from a wound or from an IV injection site of the subject, or for the detection of an infusion solution leaked from the IV injection site of the subject. In some cases, the infusion solution comprises a therapeutic drug (e.g., a chemotherapeutic agent).

In another aspect, the present disclosure is directed to a system for detecting a fluid leaked from a target site of a subject.

Figure 4A:
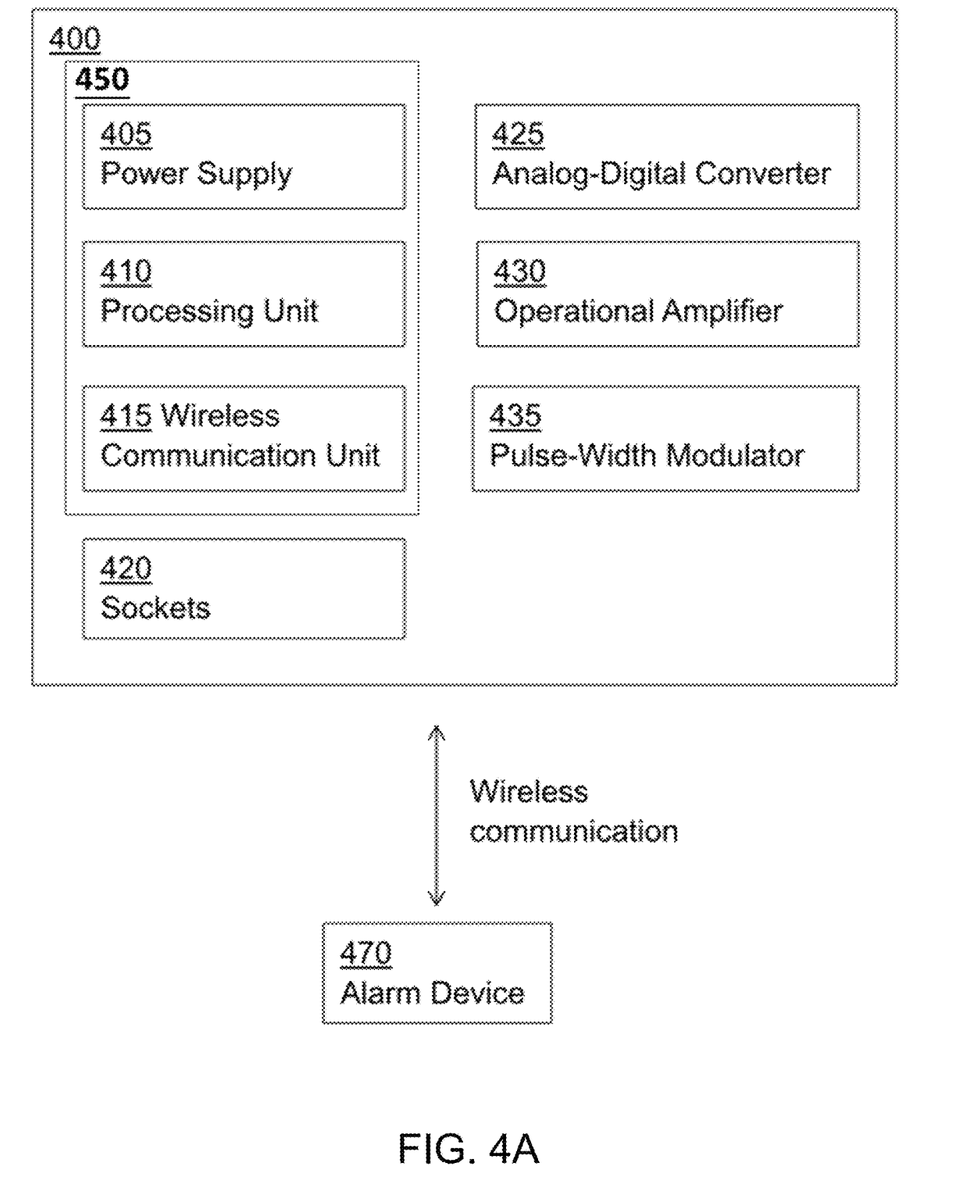

According to one embodiment of the present disclosure, the detection system comprises a sensor patch 100 of FIG. 1, and a wearable detection device 400 and an alarm device 440, as illustrated in the block diagram in FIG. 4A.

The wearable detection device 400 comprises a power supply 405, a processing unit 410, and a wireless communication unit 415.

The processing unit 410 is electrically coupled to the power supply 405 and the respective first ends 121A and 121B of the sensors 120A and 120B of the sensor patch 100. According to certain embodiments of the present disclosure, the processing unit 410 further comprises two sockets 420 that accommodate the first and second connectors 130A and 130B, respectively, so as to establish the electric connection between the processing unit 410 and the first and second detecting units 127 and 128. As could be appreciated, the processing unit 410 can be electrically coupled with the respective first ends 121A and 121B of the sensors 120A and 120B of the sensor patch 100 without using the first and second connectors 130A and 130B and the sockets 420. For example, the first ends 121A and 121B can directly contact the processing unit 410, thereby forming the electrical connection therebetween. Alternatively, the first ends 121A and 121B and the processing unit 410 can be electrically coupled indirectly via suitable connecting means other than the afore-mentioned first and second connectors 130A and 130B, and sockets 410.

During use, the conduction of the first pair of sensors 120A of the first detecting unit 127 gives rise to a first electric signal, while the conduction of the second pair of sensors 120B of the second detecting unit 128 gives rise to a second electric signal. The processing unit 410 is configured to receive the first and second electric signals respectively from the first detecting unit 127 and the second detecting unit 128. The processing unit 410 is also configured to determine the respective impedances of the first and second electric signals. Further, the processing unit 410 is configured to determine whether there is a fluid leakage condition based on the first and/or second electric signals. Specifically, the processing unit 410 is configured to generate a leak signal when (1) the first electric signal is no less than a pre-determined threshold value, and (2) the second electric signal is less than the pre-determined threshold value or the second electric signal is absent.

Persons having ordinary skill in the art could appreciate that the sensors may be conducted due to the presence of leaked fluid, sweat, or moist around the first ends of the sensors, thereby forming a closed loop. Depending on the type of components (e.g., blood, drug-containing solution, sweat, moist, etc.) conducting the paired sensors, the impedance of the closed loop resulted therefrom would vary accordingly. Therefore, a threshold impedance that can be used in discriminating the sweat from the leaked fluid is determined empirically, which is then used to design a Wheatstone bridge. According to certain embodiments of the present disclosure, the processing unit 410 comprises a Wheatstone bridge or an equivalent thereof for determining the impedance of first and second electric signals. For example, in one example, the Wheatstone bridge is designed according to a threshold impedance of 160 K$\Omega$, which is equivalent to the impedance resulted from 0.5 mL sweat on the body surface of a human subject. In this way, when the impedance of the closed loop resulted from the conduction of the sensor pair equals to or is greater than the threshold impedance, the processing unit 410 is configured to determine that the electric signal on said closed loop is triggered by a liquid (e.g., blood or drug-containing solution) other than sweat.

According to various embodiments of the present disclosure, the processing unit 410 can be a microprocessor, microcontroller, digital signal processor, application specific integrated circuit (ASIC), or field programmable gate array (FPGA).

The wireless communication unit 415 is electrically coupled to the power supply 405 and the processing unit 410. In operation, the wireless communication unit 415 is configured to receive the leak signal from the processing unit 410 and wirelessly transmit the leak signal to the alarm device 440.

According to some embodiments of the present disclosure, the wireless communication unit 415 can be a Bluetooth module, Bluetooth smart module, near field communication (NFC) module, microelectromechanical system (MEMS)-based module, WIFI module, radio frequency (RF) module, or radio frequency identification (RFID) module.

In certain embodiments, the present wearable detection device 400 may further comprise a substrate 450, and the power supply 405, the processing unit 410, the wireless communication unit 415, and the sockets 420, as well as other optional elements described below, are surface mounted on the substrate 450.

For example, the present wearable detection device 400 may further comprise an analog to digital converter 425. The analog to digital converter 425 is used to convert an as-received signal or a processed signal (e.g., by a processing circuit or any other element described herein) that is in the analog form into a digital signal. In certain embodiments, the analog to digital converter 425 is configured to convert the first electric signal or the first and second electric signals into a third electric signal; and the processing unit 410 is configured to determine the output voltage (Vo) of the third electric signal, and determine the type of the leaked liquid based on the output voltage.

According to optional embodiments, the present wearable detection device 400 may further comprise an operational amplifier 430. The operational amplifier 430 is used to amplify an as-received signal or a processed signal (e.g., by a processing circuit or any other element described herein), thereby increasing the detection sensitivity of the wearable detection device 400.

Still optionally, present wearable detection device 400 may further comprise a pulse-width modulator (PWM) 435. The pulse-width modulator 435 is used, together with a timer, to adjust the duty cycle of the wearable detection device 400, thereby substantially decreasing the power consumption of the wearable detection device 400.

In certain embodiments, the present power supply 405 comprises a battery.

Optionally, the wearable detection device 400 may have a casing (not illustrated in FIG. 4A), and all the elements constituting the wearable detection device 400 are enclosed in the casing.

The alarm device 440 is communicatively coupled to the wireless communication unit 415. During use, the alarm device 440 is configured to receive the leak signal sent from the wireless communication unit 415, and in turn, generate an alarm to notify a user (such as a health caretaker or the subject) about the fluid leakage.

In certain embodiments, the alarm device 440 can be a multimeter, personal digital assistant (PDA), personal computer (PC), notebook, tablet computer, or smart phone.

According to various embodiments of the present disclosure, the alarm device 470 can generate a sound, voice, text, icon, light, and/or vibration to alert the user upon receiving the leak signal.

In certain embodiments, the present alarm device 440 may further comprise a user interface (not shown in FIG. 4A), which is configured to present the alarm to a user and/or receive an input from the user. For example, the alarm device 440 may comprises a display (not shown in FIG. 4A) for rendering the user interface, and the alarm can be presented as a pop-up window containing a text or graphic prompt.

Figure 4B:
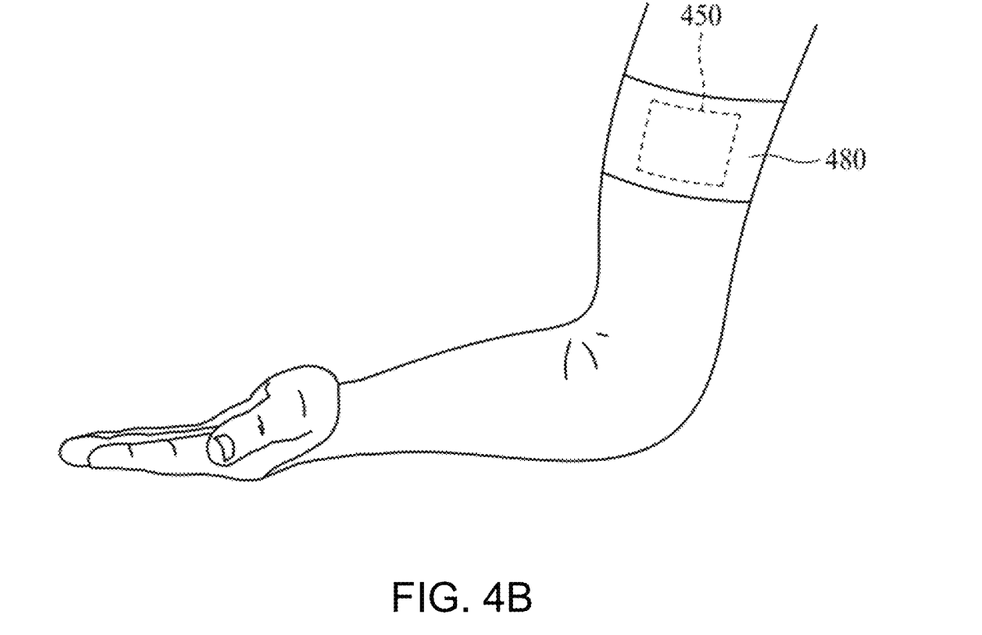

In some embodiments, the present detection system may further comprise a carrier 480 as illustrated in FIG. 4B, in which the carrier 480 is configured to accommodate the wearable detection device 400, and be worn around a suitable body part of the subject. For example, the carrier 480 may be optionally disposed with a pocket, a hole, or a recess to accommodate the wearable detection device 400. Alternatively, the carrier 480 is supplied with a fixing element such as a latch or hook fibers (e.g., VELCO®) so that the wearable detection device 400 with a corresponding fixing elements can be attached to the carrier 480.

According to carious embodiments of the present disclosure, the carrier 480 can be manufactured as a wristband or an armband. In this case, the wristband or an armband can wrap around the wrist or arm of the subject as illustrated in FIG. 4B. As could be appreciated, the carrier 480 could also be worn around any other suitable body part, such as the ankle, foot, leg, hand, head, neck, chest, abdomen, or hip.

Alternatively, the wearable detection device 400 is secured on to the subject's skin by use of a medical tape or an elastic band.

In still another aspect, the present disclosure is directed to a method for detecting a fluid leakage occurring at a target site of a subject. Said detection method employs the detection system according to the above aspect/embodiments of the present disclosure.

Prior to the commencement of the present detection method, a health caretaker applies the sensor patch (e.g., the sensor patch 100 of FIG. 1) onto a subject's body. Specifically, the respective first ends 121A of the first pair of sensors 120A are placed at a first position approximating the target site, while the respective first ends 121B of the second pair of sensors 120B are placed at a second position that is away from the target site; thereafter or at the same time, the first and second detecting units 127 and 128 are secured at their respective first and second positions by the adhesive surface 104 of the sensor patch body 110. Also, the wearable detection device (e.g., the wearable detection device 400 of FIG. 4A) is disposed on a suitable body part of the subject, and the first and second connectors 130A and 130B are respectively inserted into the two sockets 420, thereby establishing the electrical connection between the sensor patch 100 and the wearable detection device 400.

According to various embodiments of the present disclosure, the detection method comprises the steps as follows. The first electric signal transmitted from the first detecting unit 127 and/or the second electric signal transmitted from the second detecting unit 128 is (are) received by the processing unit 410. The first and/or second electric signal is processed by the processing unit 410 to determine the impedance of the first and/or second electric signal. A leak signal is generated by the processing unit 410 when (1) the impedance of the first electric signal is no less than a threshold, and (2) the impedance of the second electric signal is less than the threshold or the second electric signal is absent. The leak signal is wirelessly transmitted to the alarm device 470 by the wireless communication unit 415. An alarm (e.g., a sound, voice, text, icon, light, and/or vibration) is made by the alarm device 470 based on the leak signal, so as to notify a user about the fluid leakage condition occurring at the target site.

According to various embodiments of the present disclosure, the present detection method can be used to detect blood leakage occurring at the wound or injection site of the subject, or the leakage of an infusion solution occurring at the injection site of the subject. In some cases, the infusion solution comprises a therapeutic drug.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE 1

In the following examples, the present wearable detection device was constructed using the CC2540 Bluetooth chip (purchased from Texas Instruments) with a programmable 8051 microprocessor. To achieve a compact size (18*11*4 mm), the elements were surface mounted on both sides of the chip. The average Bluetooth transmission distance of the present wearable detection device was about 10 to 50 meters. The chip was powered by a CR 2032 battery (220 mAh); and the average battery life was about 3,241 minutes while operating with a transmission rate of one time per second.

To determine the distance D between the first ends of two sensors in one sensor pair, a sensor patch with only one sensor pair was affixed to the subject's forearm in the supinated position; the first ends of the two sensors were spaced apart by 2.5, 5, or 10 millimeters (n =3), respectively. The second ends of the two sensors were coupled with a connector, which was coupled to the socket on the wearable detection device. Thereafter, 1 c.c. of blood was slowly injected to a target site in close proximity to the first ends of the two sensors using a needle; the injected volume that triggered the alarm was recorded, and the results are summarized in Table 1.

TABLE 1

| | 10 mm | 5 mm | 2.5 mm |
|---|---|---|---|
| Test 1 | Not Detectable (1 c.c.) | Detected (0.18 c.c.) | Detected (0.06 c.c.) |
| Test 2 | Not Detectable (1 c.c.) | Detected (0.21 c.c.) | False positive (0 c.c.) |
| Test 3 | Not Detectable (1 c.c.) | Detected (0.20 c.c.) | Detected (0.09 c.c.) |

The data in Table 1 demonstrated that a sensor patch with a distance D of 10 mm between the first ends of the paired sensors could not detect the presence of 1 c.c. of blood at the target site. On the other hand, a distance of 2.5 or 5 mm allowed the sensor patch to detect the presence of blood at a relatively low volume.

However, the test results also revealed that when the distance D used for detection were too close (e.g., the distance D of 2.5 mm), a false positive detection might arise therefrom. Nonetheless, the presently claimed sensor patch has two pairs of sensors, which reduce the incidences of false positive detection; and hence, according to various embodiments of the present disclosure, a sensor distance D of 2.5 mm is feasible to give suitable detection sensitivity/specificity.

EXAMPLE 2

In this example, the detection time and detectable liquid volume of the present sensor patch were determined. In three experimental groups, the first ends of the paired sensors (spaced by 5 mm) were respectively disposed above (Group 1), without (Group 2), and under (Group 3) an additional highly permeable adhesive bandage (n=3). Thereafter, the blood was slowly injected to the target site in close proximity to the first ends of the paired sensors with a needle until an alarm was given by the alarm device. The volume of blood injected when the alarm went off and time elapsed since the injection started were summarized in Table 2.

TABLE 2

|  | Group 1 | Group 2 | Group 3 |
| --- | --- | --- | --- |
| Test 1 | 35 sec. | 1 sec. | 3 sec. |
|  | 3.3 c.c. | 0.14 c.c. | 1.2 c.c. |
| Test 2 | 38 sec. | 1 sec. | 3 sec. |
|  | 3.5 c.c. | 0.15 c.c. | 1.1 c.c. |
| Test 3 | 33 sec. | 1 sec. | 3 sec. |
|  | 3.3 c.c. | 0.17 c.c. | 1.4 c.c. |

The data in Table 2 indicated that when the paired sensors were disposed above the adhesive bandage (Group 1), the present wearable detection device could only detect the occurrence of fluid leakage in the case of excessive leakage (e.g., about 3.3 to 3.5 c.c. of blood) in a delayed manner (e.g., about 33 to 35 seconds after the start time). On the other hand, if the paired sensors were directly in contact with the skin of the subject (Group 2), the blood was detectable at a relatively low volume (about 0.14 to 0.17 c.c.) and in a fast manner (1 second since the injection started). Further, the application of the adhesive bandage above the first ends of the paired sensors (Group 3) resulted in the delay of the detected time and increase of the detectable fluid volume, compared with the results of Group 2.

EXAMPLE 3

In the present example, one sensor pair was used to determine the impedance of different liquid (0.5 mL) on the body surface of a human subject. The experimental results indicated that the impedance of the blood was 520 KΩ, the impedance of 200 mg/mL glucose solution was 550 KΩ, the impedance of sweat was 160 KΩ, and the impedance of saline was 360 KΩ. The results were used as the basis for the design of the bridge circuit. In the following experiments, the threshold impedance value of the bridge circuit was 100 KΩ.

Figure 5:
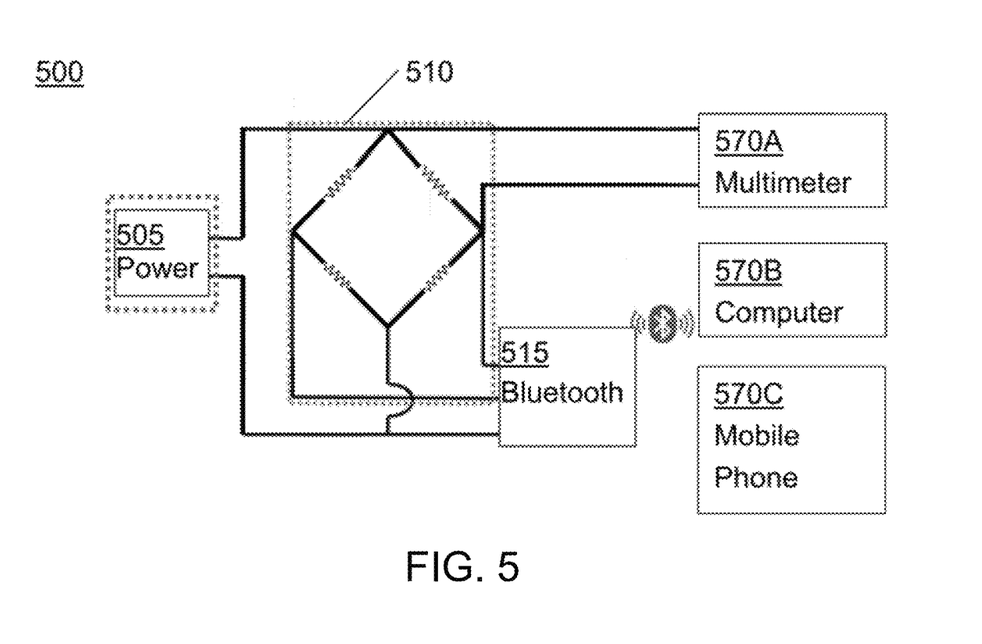
FIG. 5 is a schematic diagram illustrating a wearable detection device and an alarm device of a system according to one embodiment of the present disclosure.

Thereafter, the wearable detection device 500 illustrated in FIG. 5 and two sensor pairs were used to detect the leakage of various liquids. As illustrated in FIG. 5, the wearable detection device 500 comprises a power 505 (3 V), a bridge circuit 510 and a Bluetooth module 515. The wearable detection device 500 can be coupled with various alarm device; for example, the wearable detection device 500 can be electrically coupled with a multimeter 570A (such as a Ketheley 2000 multimeter), or the wearable detection device 500 can be communicatively coupled with a computer 570B or a mobile phone 570C via the Bluetooth module 515. A resistor of 1 MΩ is bridged to the end at which the bridge circuit 510 coupled with the second sensor pair.

The wearable detection device 500 and the sensor patch were disposed according to those set forth in Example 1, above; thereafter, 0.3 mL of various liquids and sweat were respectively injected into the sites in adjacent to the first and second locations of the first and second sensor pairs using a needle, so as to determine the analog-to-digital output value (ADC value) and output voltage (Vo) of the closed loop formed by the sweat, liquids or combinations thereof. The results are summarized in Table 3.

TABLE 3

| 1st Sensor Pair | 2nd Sensor Pair | ADC value | Output Voltage |
| --- | --- | --- | --- |
| Saline | — | 10 | 0.38 V |
| Blood | — | 8 | 0.21 V |
| Glucose Sol. | — | 6 | 0.19 V |
| Sweat | Sweat | FA | −0.10 V |
| — | — | F4 | −0.27 V |
| Saline | Sweat | DE | −0.61 V |
| Blood | Sweat | DC | −0.78 V |
| Glucose Sol. | Sweat | DA | −0.80 V |

As could be seen in Table 3, when the output voltage was in the range between −0.11 V to −0.3 V, there were no fluid leakage at the target site. On the other hand, in other groups, it was feasible to determine whether the leaked fluid was the blood, saline or glucose solution based on the detected output circuit.

EXAMPLE 4

In this example, the wearable detection device 500 described in the Example 3, above, was used together with two sensor pairs (i.e., two detecting units) in which the first ends of the respective sensor pairs were in direct contact with the skin of the subject, and the distance between the first and second locations of the two sensor pairs (the two detecting units) was 5 millimeters. Thereafter, the various liquids (blood, 200 mg/mL glucose solution and saline) and sweat were respectively injected into the sites in close proximity to the first and second locations of the first and second sensor pairs (the two detecting units) using a needle; the injected volume that triggered the alarm was recorded, and the results are summarized in Table 4.

TABLE 4

|  | Group 1 Blood/Sweat | Group 2 Glucose Sol./Sweat | Group 3 Saline/Sweat |
| --- | --- | --- | --- |
| Test 1 | 1 sec. | 1 sec. | 1 sec. |
|  | 0.2 c.c. | 0.2 c.c. | 0.2 c.c. |
| Test 2 | 1 sec. | 1 sec. | 1 sec. |
|  | 0.2 c.c. | 0.2 c.c. | 0.2 c.c. |
| Test 3 | 1 sec. | 1 sec. | 1 sec. |
|  | 0.2 c.c. | 0.2 c.c. | 0.2 c.c. |

The data in Table 4 indicated that the present system for detecting fluid leakage was capable of detecting about 0.2 c.c. of leaked fluid after 1 second of the leakage.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A sensor patch for use in a fluid leakage detection process for detecting a fluid leaked from a target site of a subject, comprising,
    a first detecting unit, comprising a first pair of sensors having first ends configured to be placed at a first position approximating the target site;

a second detecting unit, comprising a second pair of sensors having first ends configured to be placed at a second position away from the target site; and a patch body, having an adhesive surface for securing the first and second detecting units to the subject; wherein each sensor comprises a conductive wire and an insulating sheath encapsulating the conductive wire in a manner that a portion of the first end of the conductive wire is exposed without directly contacting the subject's skin.

2. The sensor patch of claim 1, wherein the first ends of the two sensors in the first or second detecting unit are spaced apart by 2.5 to 7.5 millimeters.

3. The sensor patch of claim 1, wherein the portion of the conductive wire that is exposed has a length ranging from 2.5 to 7.5 millimeters.

4. The sensor patch of claim 3, wherein the length is 5 millimeters.

5. The sensor patch of claim 1, wherein the distance between the first position and the second position is 1 to 5 centimeters.

6. The sensor patch of claim 1, wherein the thickness of the insulating sheath is 0.1 to 0.5 millimeters.

7. The sensor patch of claim 1, wherein
the first detecting unit further comprises a first connector electrically coupled to respective second ends of the first pair of sensors; and
the second detecting unit further comprises a second connector electrically coupled to respective second ends of the second pair of sensors.

8. The sensor patch of claim 1, further comprising a release sheet attached to the adhesive surface of the patch body.

9. The sensor patch of claim 1, wherein the fluid is blood or an infusion solution.

10. The sensor patch of claim 8, wherein the infusion solution comprises a therapeutic drug.

11. The sensor patch of claim 1, further comprising a frame attached to the other surface of the patch body and disposed along at least a portion of the peripheral of the patch body.

12. The sensor patch of claim 11, wherein the frame is disposed along the peripheral of the patch body.

13. The sensor patch of claim 1, wherein the patch body is made from a waterproof, transparent film.

14. The sensor patch of claim 1, wherein the patch body is air and vapor-permeable.

15. A system for detecting a fluid leaked from a target site of a subject, comprising,
the sensor patch of claim 1, in which the first detecting unit is configured to generate a first electric signal when the first pair of sensors are conducted, while the second detecting unit is configured to generate a second electric signal when the second pair of sensors are conducted;
a wearable detection device comprising,
a power supply,
a processing unit, which is electrically coupled to the power supply and the first and second detecting units, wherein the processing unit is configured to determine the respective impedances of the first and second electric signals, and generate a leak signal when (1) the impedance of the first electric signal is no less than a threshold, and (2) the impedance of the second electric signal is less than the threshold or the second electric signal is absent;
a wireless communication unit, which is electrically coupled to the power supply and the processing unit, and is configured to send out the leak signal generated by the processing unit; and
an alarm device, which is communicatively coupled to the wireless communication unit and is configured to generate an alarm upon receiving the leak signal sent from the wireless communication unit.

16. The system of claim 15, wherein
the first detecting unit further comprises a first connector electrically coupled to the respective second ends of the first pair of sensors;
the second detecting unit further comprises a second connector electrically coupled to the respective second ends of the second pair of sensors; and
the wearable detection device further comprises two sockets for respectively accommodating the first and second connectors.

17. The system of claim 15, wherein the wearable detection device further comprises a substrate on which the power supply, the processing unit, and the wireless communication unit are surface mounted.

18. The system of claim 15, wherein the wearable detection device further comprises an analog to digital converter that is electrically coupled with the processing unit.

19. The system of claim 18, wherein
the digital converter is configured to convert the first electric signal or the first and second electric signals into a third electric signal; and
the processing unit is configured to determine an output voltage of the third electric signal, and determine a type of the liquid that is leaked based on the output voltage.

20. The system of claim 15, wherein the wearable detection device further comprises an operational amplifier that is electrically coupled with the processing unit.

21. The system of claim 15, wherein the wearable detection device further comprises a pulse-width modulator that is electrically coupled with the processing unit.

22. The system of claim 15, wherein the processing unit is a microprocessor, microcontroller, digital signal processor, application specific integrated circuit (ASIC), or field programmable gate array (FPGA).

23. The system of claim 15, wherein the wireless communication unit is a Bluetooth module, Bluetooth smart module, near field communication (NFC) module, microelectromechanical system (MEMS)-based module, WIFI module, radio frequency (RF) module or radio frequency identification (RFID) module.

24. The system of claim 15, wherein the alarm device is a multimeter, personal digital assistant (PDA), personal computer, notebook, tablet computer, or smart phone.

25. The system of claim 15, wherein the alarm device further comprises a user interface, configured to present the alarm to a user and/or receive an input from the user.

26. The system of claim 15, further comprising a carrier, configured to accommodate the wearable detection device, and be worn around a body part of the subject.

27. A method for detecting a fluid leaked from a target site of a subject by use of the system of claim 15, wherein the respective first ends of the first pair of sensors are placed at the first position, the respective first ends of the second pair of sensors are placed at the second positon that is away from the target site, and the wearable detection device is worn by the subject, and the method comprises:
determining the respective impedances of the first and/or second electric signals by use of the processing unit;

generating a leak signal by use of the processing unit, when (1) the impedance of the first electric signal is no less than a threshold, and (2) the impedance of the second electric signal is less than the threshold or the second electric signal is absent;

transmitting the leak signal to the alarm device by use of the wireless communication unit; and generating an alarm by use of the alarm device based on leak signal.

28. The method of claim 27, wherein the fluid is blood or an infusion solution.

29. The method of claim 28, wherein the infusion solution comprises a therapeutic drug.

\* \* \* \* \*